US011503982B2

(12) United States Patent
Yamasaki et al.

(10) Patent No.: US 11,503,982 B2
(45) Date of Patent: Nov. 22, 2022

(54) IMAGE PROCESSING APPARATUS, IMAGE PROCESSING METHOD, AND COMPUTER-READABLE RECORDING MEDIUM FOR DETECTING A DEFECTIVE PIXEL IN AN IMAGE FRAME

(71) Applicant: OLYMPUS CORPORATION, Tokyo (JP)

(72) Inventors: Teruaki Yamasaki, Hino (JP); Hiroki Maruyama, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 195 days.

(21) Appl. No.: 16/987,698

(22) Filed: Aug. 7, 2020

(65) Prior Publication Data

US 2020/0359875 A1 Nov. 19, 2020

Related U.S. Application Data

(63) Continuation of application No. PCT/JP2019/014267, filed on Mar. 29, 2019.

(30) Foreign Application Priority Data

Apr. 6, 2018 (JP) .............................. JP2018-073663

(51) Int. Cl.
*A61B 1/00* (2006.01)
*G06T 7/00* (2017.01)
(Continued)

(52) U.S. Cl.
CPC ........ *A61B 1/00057* (2013.01); *G06T 7/0012* (2013.01); *G06T 7/20* (2013.01);
(Continued)

(58) Field of Classification Search
None
See application file for complete search history.

(56) References Cited

U.S. PATENT DOCUMENTS 9,161,029 B1 * 10/2015 Kumar .................. G06T 7/0002
2002/0149683 A1 * 10/2002 Post ..................... H04N 5/2176
348/E5.081
(Continued)

FOREIGN PATENT DOCUMENTS

JP 2002-354340 A 12/2002
JP 2006-060550 A 3/2006
(Continued)

OTHER PUBLICATIONS

X. Wang and M. Mirmehdi, "Archive Film Defect Detection and Removal: An Automatic Restoration Framework," in IEEE Transactions on Image Processing, vol. 21, No. 8, pp. 3757-3769, Aug. 2012 (Year: 2012).*

(Continued)

*Primary Examiner* — Gandhi Thirugnanam
(74) *Attorney, Agent, or Firm* — Scully, Scott, Murphy & Presser, P.C.

(57) ABSTRACT

An image processing apparatus includes a processor including hardware. The processor is configured to: calculate a motion evaluation value on a motion of a subject in a determination target frame; acquire a difference evaluation value of the determination target frame; determine whether to perform defective pixel detection on an image of the determination target frame by using the motion evaluation value and the difference evaluation value; and when it is determined that the defective pixel detection is to be performed, detect a defective pixel by determining whether a pixel of interest that is a determination target is a defective pixel with respect to the image of the determination target frame, based on a pixel value of the pixel of interest and (Continued)

pixel values of neighboring pixels that are located in a vicinity of the pixel of interest.

7 Claims, 6 Drawing Sheets

(51) Int. Cl.
  *G06T 7/20* (2017.01)
  *H04N 5/367* (2011.01)
(52) U.S. Cl.
  CPC ... *H04N 5/367* (2013.01); *G06T 2207/10068* (2013.01); *G06T 2207/30004* (2013.01)

(56) References Cited

U.S. PATENT DOCUMENTS

| | | | |
|---|---|---|---|
| 2002/0176013 A1* | 11/2002 | Itoh | H04N 5/367 348/E5.081 |
| 2006/0215046 A1* | 9/2006 | Tibi | F41G 7/001 348/246 |
| 2008/0106619 A1* | 5/2008 | Sumiya | H04N 5/3675 348/E9.037 |
| 2009/0174808 A1* | 7/2009 | Mochida | G03B 7/28 348/148 |
| 2010/0066868 A1* | 3/2010 | Shohara | H04N 5/217 348/241 |
| 2010/0165087 A1* | 7/2010 | Corso | A61B 1/05 348/E5.093 |
| 2014/0375846 A1* | 12/2014 | Toyoda | G06T 5/002 348/241 |
| 2016/0105591 A1* | 4/2016 | Theis | G06T 5/50 382/275 |
| 2016/0241800 A1* | 8/2016 | Shin | G02B 23/2484 |
| 2018/0109745 A1* | 4/2018 | Maruyama | H04N 1/409 |
| 2019/0149757 A1* | 5/2019 | Yamasaki | H04N 1/40 348/247 |
| 2020/0029020 A1* | 1/2020 | Morales | H04N 5/3577 |
| 2020/0359875 A1* | 11/2020 | Yamasaki | H04N 5/367 |

FOREIGN PATENT DOCUMENTS

| | | |
|---|---|---|
| JP | 2007-049529 A | 2/2007 |
| JP | 2009-157087 A | 7/2009 |
| JP | 2007-150895 A | 6/2014 |
| WO | 2017/221376 A1 | 12/2017 |

OTHER PUBLICATIONS

Sheikh Shanawaz Mostafa, L. Natércia Sousa, Nuno Fábio Ferreira, Ricardo M. Sousa, Joao Santos, Martin Wäny, and F. Morgado-Dias "Full image-processing pipeline in field-programmable gate array for a small endoscopic camera," Journal of Electronic Imaging 26(1), 013005 (Jan. 11, 2017). (Year: 2017).*

International Search Report dated May 28, 2019 received in PCT/JP2019/014267.

* cited by examiner

FIG.3

|  |  | MOTION EVALUATION VALUE | |
|---|---|---|---|
|  |  | 0 | 1≤VALUE |
| DIFFERENCE EVALUATION VALUE | 0 | MOTIONLESS | FLAT |
|  | 1≤VALUE | - | MOVING |

FIG.4

|    |    |    |
|----|----|----|
| p1 | p2 | p3 |
| p4 | pt | p5 |
| p6 | p7 | p8 |

FIG.5

| a1  | a2  | a3  | a4  | a5  |
| a6  | p1  | p2  | p3  | a7  |
| a8  | p4  | pt  | p5  | p9  |
| a10 | p6  | p7  | p8  | a11 |
| a12 | a13 | a14 | a15 | a16 |

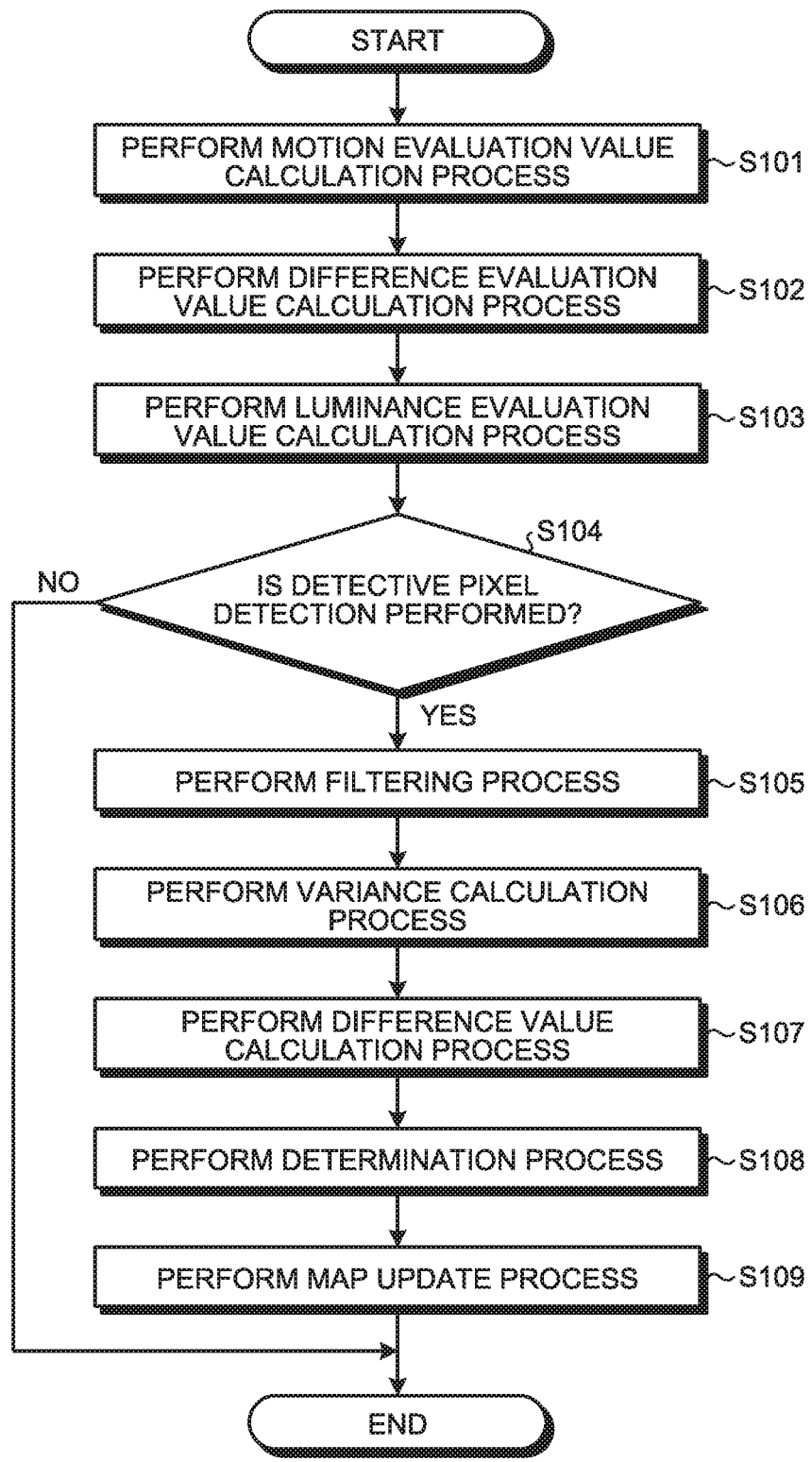

IMAGE PROCESSING APPARATUS, IMAGE PROCESSING METHOD, AND COMPUTER-READABLE RECORDING MEDIUM FOR DETECTING A DEFECTIVE PIXEL IN AN IMAGE FRAME

CROSS-REFERENCE TO RELATED APPLICATIONS

This application is a continuation of PCT international application Ser. No. PCT/JP2019/014267, filed on Mar. 29, 2019 which designates the United States, incorporated herein by reference, and which claims the benefit of priority from Japanese Patent Applications No. 2018-073663, filed on Apr. 6, 2018, incorporated herein by reference.

BACKGROUND

1. Technical Field

The present disclosure relates to an image processing apparatus, an image processing method, and a computer-readable recording medium.

2. Related Art

In the related art, in the medical field, an endoscope system is used to observe inside of a subject. An endoscope generally captures an in-vivo image by inserting a flexible insertion portion that has a thin and elongated shape into a subject, such as a patient, causing illumination light supplied by a light source device to be emitted from a distal end of the insertion portion, and causing an imaging unit at the distal end of the insertion portion to receive reflected light of the illumination light. The in-vivo image captured by the imaging unit of the endoscope is subjected to predetermined image processing by a processing device of an endoscope system, and displayed on a display of the endoscope system. A user, such as a doctor, observes an organ of the subject on the basis of the in-vivo image displayed on the display.

The imaging unit is configured with a solid-state image sensor in which a plurality of pixels for performing photoelectric conversion on received light are arranged in a matrix manner. In the solid-state image sensor, a pixel defect may occur due to radiation present in nature, fine dust, a foreign matter during film formation, or the like. As a technology for detecting the pixel defect, a technology has been proposed in which candidate defective pixels are detected using information on a pixel of interest and neighboring pixels, an evaluation value is calculated for each of frames with respect to a detection result, and whether the candidate defective pixels are determined as defective pixels on the basis of the evaluation values (see, for example, International Publication No. WO 2017/221376)

SUMMARY

In some embodiments, provided is an image processing apparatus that performs a process on an image that is captured by an endoscope introduced in a subject. The image processing apparatus includes a processor including hardware, the processor being configured to: calculate, based on images of a plurality of frames, a motion evaluation value on a motion of a subject in a determination target frame by using an image of the determination target frame and an image of a frame for which an acquisition time is different from an acquisition time of the determination target frame; calculate a difference between a pixel value in the image of the determination target frame and a pixel value in the image of the frame for which the acquisition time is different from the acquisition time of the determination target frame to acquire a difference evaluation value of the determination target frame; determine whether to perform defective pixel detection on the image of the determination target frame by using the motion evaluation value and the difference evaluation value; and when it is determined that the defective pixel detection is to be performed, detect a defective pixel by determining whether a pixel of interest that is a determination target is a defective pixel with respect to the image of the determination target frame, based on a pixel value of the pixel of interest and pixel values of neighboring pixels that are located in a vicinity of the pixel of interest.

In some embodiments, provided is an image processing method of performing a process on an image that is captured by an endoscope introduced into a subject. The image processing method includes: calculating, based on images of a plurality of frames, a motion evaluation value on a motion of a subject in a determination target frame by using an image of the determination target frame and an image of a frame for which an acquisition time is different from an acquisition time of the determination target frame; calculating a difference between a pixel value in the image of the determination target frame and a pixel value in the image of the frame for which the acquisition time is different from the acquisition time of the determination target frame to acquire a difference evaluation value of the determination target frame; determining whether to perform defective pixel detection on the image of the determination target value by using the motion evaluation value and the difference evaluation value; and in a case where it is determined that the defective pixel detection is to be performed at the determining, detecting a defective pixel by determining whether a pixel of interest that is a determination target is a defective pixel with respect to the image of the determination target frame, based on a pixel value of the pixel of interest and pixel values of neighboring pixels that are located in a vicinity of the pixel of interest.

In some embodiments, provided is a non-transitory computer-readable recording medium with an executable program stored thereon. The program causes an image processing apparatus configured to perform a process on an image that is captured by an endoscope introduced in a subject, to execute: calculating, based on images of a plurality of frames, a motion evaluation value on a motion of a subject in a determination target frame by using an image of the determination target frame and an image of a frame for which an acquisition time is different from an acquisition time of the determination target frame; calculating a difference between a pixel value in the image of the determination target frame and a pixel value in the image of the frame for which the acquisition time is different from the acquisition time of the determination target frame to acquire a difference evaluation value of the determination target frame; determining whether to perform defective pixel detection on the image of the determination target value by using the motion evaluation value and the difference evaluation value; and in a case where it is determined that the defective pixel detection is to be performed at the determining, detecting a defective pixel by determining whether a pixel of interest that is a determination target is a defective pixel with respect to the image of the determination target frame, based on a pixel value of the pixel of interest and pixel values of neighboring pixels that are located in a vicinity of the pixel of interest.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 3 is a diagram for explaining execution determination performed by a motionlessness determination unit of a processing device according to one embodiment of the present disclosure.

FIG. 4 is a diagram for explaining a filtering process performed by a filtering processing unit of the processing device according to one embodiment of the present disclosure.

FIG. 5 is a diagram for explaining the filtering process performed by the filtering processing unit of the processing device according to one embodiment of the present disclosure.

FIG. 8 is a flowchart illustrating image processing performed by the processing device according to one embodiment of the present disclosure.

DETAILED DESCRIPTION

Modes (hereinafter, referred to as "embodiments") for carrying out the present disclosure will be described below. In the embodiments, as one example of a system that includes an image processing apparatus according to the present disclosure, a medical endoscope system that captures an image of inside of a subject, such as a patient, and displays the image will be described. Further, the present disclosure is not limited by the embodiments. Furthermore, in description of the drawings, the same components will be denoted by the same reference symbols.

Figure 1:
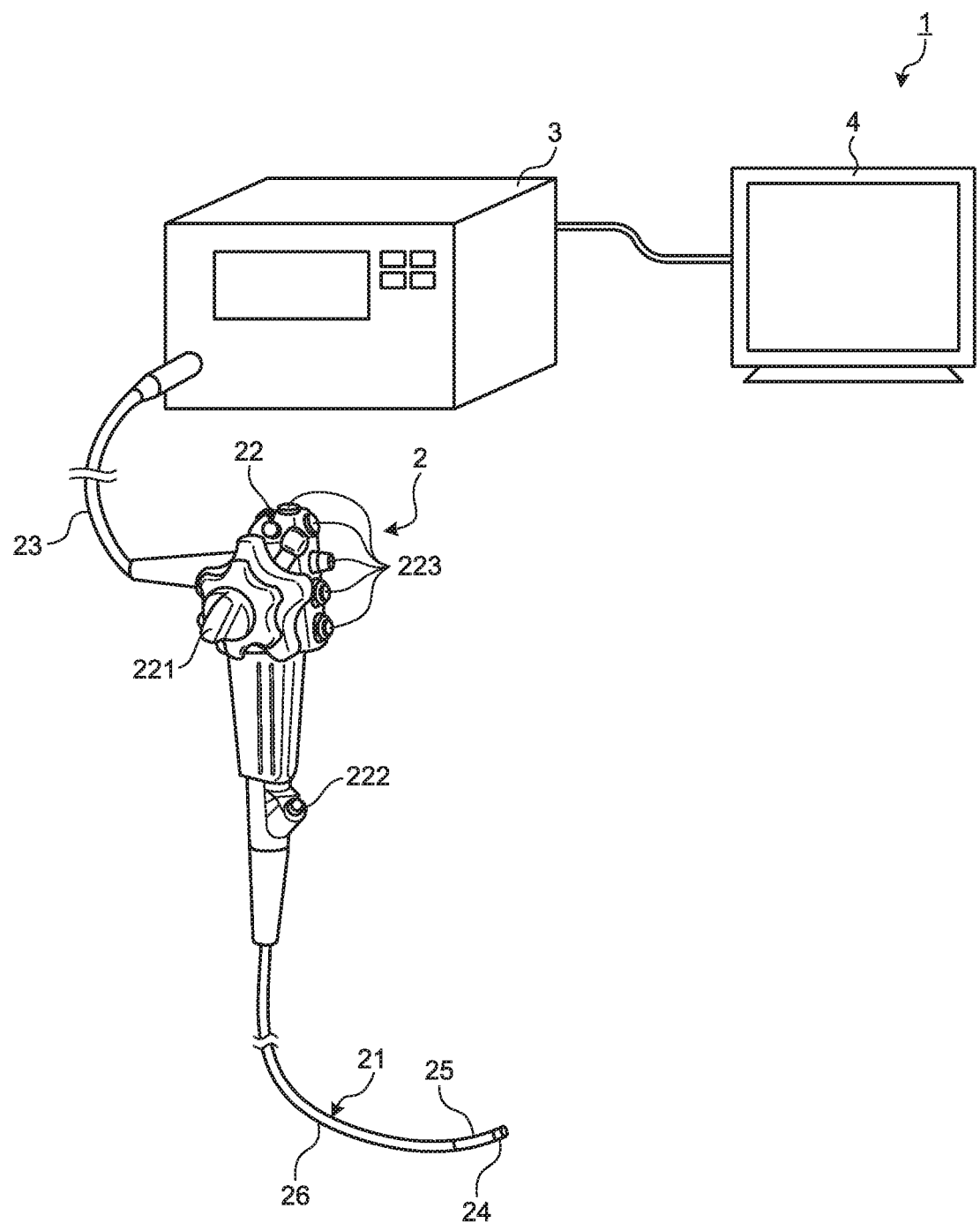
FIG. 1 is a diagram illustrating a schematic configuration of an endoscope system according to one embodiment of the present disclosure.
Figure 2:
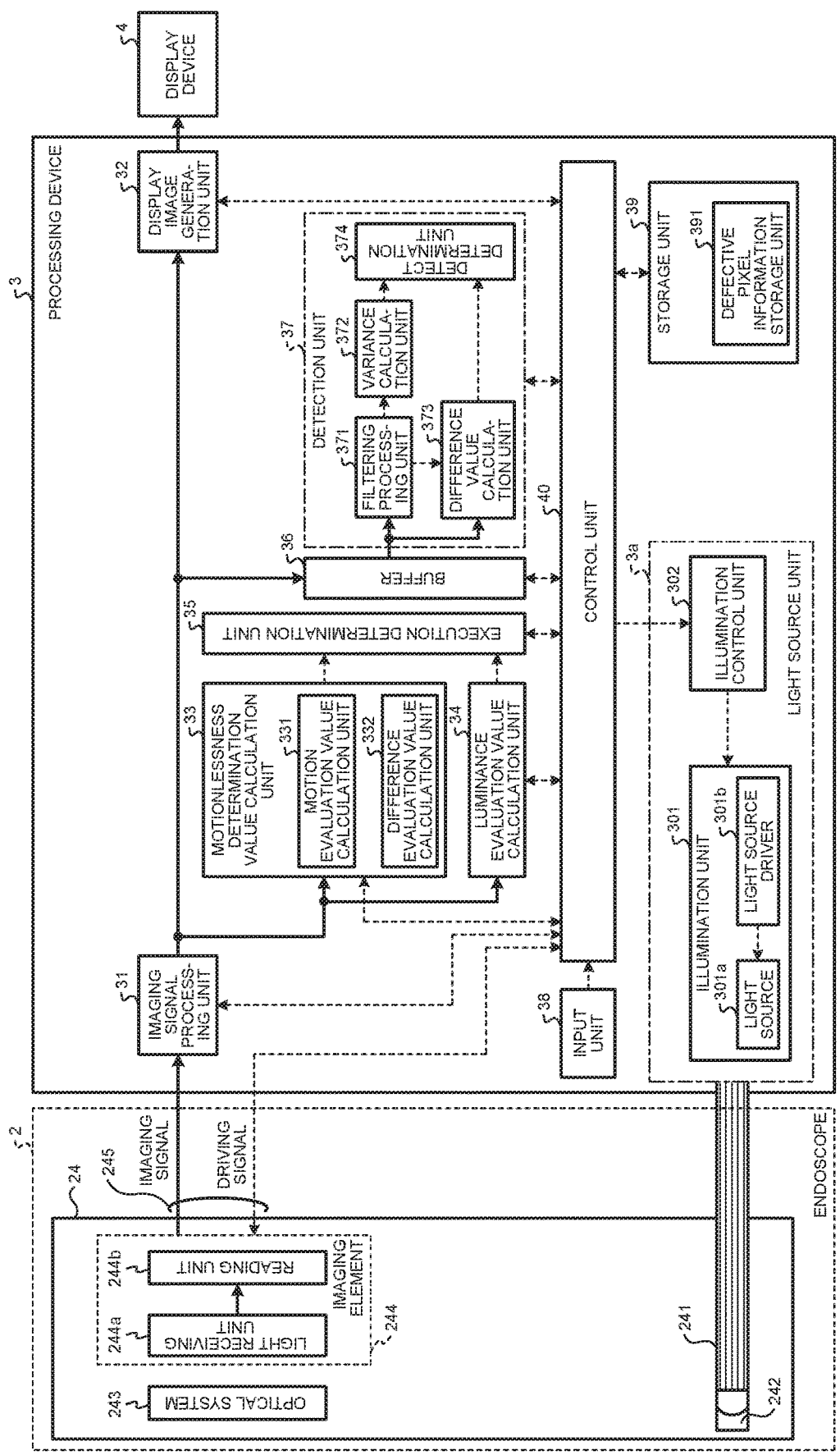
FIG. 2 is a block diagram illustrating a schematic configuration of the endoscope system according to one embodiment of the present disclosure.

FIG. 1 is a diagram illustrating a schematic configuration of an endoscope system according to one embodiment of the present disclosure. FIG. 2 is a block diagram illustrating a schematic configuration of the endoscope system according to the embodiment.

An endoscope system 1 illustrated in FIG. 1 and FIG. 2 includes an endoscope 2, a distal end portion of which is inserted into a subject and which captures an image of inside of the subject (hereinafter, also referred to as an in-vivo image), a processing device 3 that includes a light source unit 3a for generating illumination light to be emitted from a distal end of the endoscope 2, that performs predetermined signal processing on an imaging signal captured by the endoscope 2, and that comprehensively controls entire operation of the endoscope system 1, and a display device 4 that displays the in-vivo image generated through the signal processing performed by the processing device 3.

The endoscope 2 includes a flexible insertion portion 21 that has a thin and elongated shape, an operation unit 22 that is connected to a proximal end side of the insertion portion 21 and that receives input of various operation signals, and a universal cord 23 that extends from the operation unit 22 in a direction different from a direction in which the insertion portion 21 extends and that has various built-in cables connected to the processing device 3 (including the light source unit 3a).

The insertion portion 21 includes a distal end portion 24 that includes a built-in imaging element 244, in which pixels that receive light and generate signals by performing photoelectric conversion on the light are arranged two-dimensionally, a bending portion 25 that includes a plurality of bending pieces and that is freely bendable, and a flexible tube portion 26 that is connected to a proximal end side of the bending portion 25, that is flexible, and that has an elongated shape. The insertion portion 21 is inserted in a body cavity of the subject and captures, by the imaging element 244, an image of an object, such as a living tissue, that is located at a position where external light does not reach.

The distal end portion 24 includes a light guide 241 that is configured with fiberglass or the like and serves as a light guide path for light emitted by the light source unit 3a, an illumination lens 242 that is arranged at a distal end of the light guide 241, an optical system 243 that condenses light, and the imaging element 244 (imaging unit) that is arranged at an image forming position of the optical system 243, that receives light condensed by the optical system 243, that performs photoelectric conversion on the light to obtain an electrical signal, and that performs predetermined signal processing on the electrical signal.

The optical system 243 is configured with one or more lenses, and has an optical zoom function to change an angle of view and a focus function to change a focal point.

The imaging element 244 performs photoelectric conversion on light coming from the optical system 243 and generates an electrical signal (imaging signal). Specifically, the imaging element 244 includes a light receiving unit 244a that includes a plurality of pixels, each of which includes a photodiode for accumulating charges corresponding to light intensity and a capacitor for converting charges transferred from the photodiode into voltage levels, which are arranged in a matrix manner, and each of which performs photoelectric conversion on light coming from the optical system 243 to generate an electrical signal, and a reading unit 244b that sequentially reads electrical signals generated by pixels that are arbitrarily set as read targets among the plurality of pixels included in the light receiving unit 244a, and outputs the electrical signals as imaging signals. The light receiving unit 244a includes a color filter, and each of the pixels receives light of any of wavelength bands of a plurality of color components, such as red (R), green (G), and blue (B). The imaging element 244 controls various kinds of operation of the distal end portion 24 in accordance with a driving signal received from the processing device 3. The imaging element 244 is realized by using, for example, a charge coupled device (CCD) image sensor or a complementary metal oxide semiconductor (CMOS) image sensor. Further, the imaging element 244 may be a single-chip image sensor or may include a plurality of image sensors, such as a three-chip system.

The operation unit 22 includes a bending knob 221 that causes the bending portion 25 to bend in a vertical direction and in a horizontal direction, a treatment tool insertion portion 222 for inserting a treatment tool, such as a biopsy forceps, an electric scalpel, and an inspection probe, into a body cavity of the subject, and a plurality of switches 223 that are operation input units for inputting operation instruction signals for peripheral devices, such as an air supply unit, a water supply unit, and a screen display control, in addition to the processing device 3. The treatment tool inserted from the treatment tool insertion portion 222 is exposed from an opening portion (not illustrated) through a treatment tool channel (not illustrated) of the distal end portion 24.

The universal cord 23 incorporates at least the light guide 241 and an assembly cable 245 in which one or more signal lines are assembled. The assembly cable 245 includes a signal line for transferring an imaging signal, a signal line for transferring a driving signal for driving the imaging element 244, and a signal line for transmitting and receiving information including unique information on the endoscope 2 (the imaging element 244). Meanwhile, in the present embodiment, it is explained that electrical signals are transferred using the signal lines, but it may be possible to transfer optical signals, or it may be possible to transfer signals between the endoscope 2 and the processing device 3 via radio communication.

Next, a configuration of the processing device 3 will be described. The processing device 3 includes an imaging signal processing unit 31, a display image generation unit 32, a motionlessness determination value calculation unit 33, a luminance evaluation value calculation unit 34, an execution determination unit 35, a buffer 36, a detection unit 37, an input unit 38, a storage unit 39, and a control unit 40. Meanwhile, the image processing apparatus according to the present disclosure is configured with at least the imaging signal processing unit 31, the motionlessness determination value calculation unit 33, the luminance evaluation value calculation unit 34, the execution determination unit 35, and the detection unit 37.

The imaging signal processing unit 31 receives, from the endoscope 2, an imaging signal as image data of an endoscopic image captured by the imaging element 244. Upon receiving an analog imaging signal from the endoscope 2, the imaging signal processing unit 31 performs analog-to-digital (A/D) conversion on the analog imaging signal and generates a digital imaging signal. Further, upon receiving an imaging signal as an optical signal from the endoscope 2, the imaging signal processing unit 31 performs photoelectric conversion on the imaging signal and generates a digital imaging signal.

The imaging signal processing unit 31 performs preprocessing, such as pixel defect correction, optical correction, color correction, or optical rack subtraction, on the imaging signal input from the endoscope 2, and performs signal processing, such as noise reduction, white balance adjustment, or an interpolation process, and a commonalization process for adjusting luminance of RGB to a pre-set format, on a signal generated through the pre-processing. The pixel defect correction is performed to give a pixel value to a correction target pixel (defective pixel) by referring to defective pixel information (defective pixel map) stored in the storage unit 39. Specifically, the imaging signal processing unit 31 calculates, for example, an average value or a mode value from pixel values of pixels (excluding the defective pixel) around the correction target pixel, and gives the calculated value as the pixel value. The optical correction is performed to correct optical distortion or the like of a lens. The color correction is performed to correct color temperature or color deviation. The imaging signal processing unit 31 generates a processed imaging signal (hereinafter, also simply referred to as an imaging signal) including an in-vivo image generated through the signal processing as described above. The imaging signal processing unit 31 inputs the generated processed imaging signal to the display image generation unit 32. The imaging signal processing unit 31 is configured with a general-purpose processor, such as a central processing unit (CPU), or a dedicated processor including various arithmetic circuits, such as an application specific integrated circuit (ASIC), that execute specific functions.

The display image generation unit 32 generates an image signal to be displayed by performing signal processing on a signal input from the imaging signal processing unit 31 so as to obtain a signal in a certain mode that is displayable on the display device 4. Specifically, the display image generation unit 32 performs a zoom process, an enhancement process, a compression process, or the like on the image signal and generates an endoscopic image to be displayed. If the input signal is divided into color components of RGB, the display image generation unit 32 performs an interpolation process on each of the color components and generates an image signal in which RGB color components are given at each of pixel positions. The display image generation unit 32 transmits an image signal to be displayed, which includes the generated image to be displayed, to the display device 4. The display image generation unit 32 is configured with a general-purpose processor, such as a CPU, or a dedicated processor including various arithmetic circuits, such as an ASIC, that execute specific functions.

The motionlessness determination value calculation unit 33 calculates a determination value for determining whether a subject in the image (in-vivo image) is motionless. The motionlessness determination value calculation unit 33 includes a motion evaluation value calculation unit 331 and a difference evaluation value calculation unit 332. The motionlessness determination value calculation unit 33 is configured with a general-purpose processor, such as a CPU, or a dedicated processor including various arithmetic circuits, such as an ASIC, that execute specific functions.

The motion evaluation value calculation unit 331 calculates, by using an in-vivo image of a frame for which determination is performed (hereinafter, also referred to as a determination target frame) and an in-vivo image of a frame for which an acquisition time is earlier than the determination target frame (for example, one frame earlier) (hereinafter, also referred to as a previous frame), a motion vector of a subject in the determination target frame with respect to the previous frame, and adopts a magnitude of the vector as a motion evaluation value. The motion evaluation value may be a length of vector, the number of pixels at which the vector is extended, or the like. The motion evaluation value calculation unit 331 may calculate a local motion vector for estimating movement in a vertical direction and in a horizontal direction by performing matching between the frames, or may calculate a global motion vector in which factors of movement of a focal distance, horizontal oscillation of the distal end portion 24, and vertical oscillation of the distal end portion 24 are included in addition to the local motion vector. For example, the motion evaluation value calculation unit 331 searches for the same block as a block of interest in the in-vivo image of the determination target from the in-vivo image of the previous frame by using block matching, and calculates the motion vector. Here, the block of interest is formed of a pixel of interest and neighboring pixels of the pixel of interest among pixels included in the in-vivo image.

The difference evaluation value calculation unit 332 calculates a difference value between pixel values (luminance values) at the same coordinates in the in-vivo image of the determination target frame and the in-vivo image of the previous frame for each of pixels (coordinates), and counts the number of coordinates at which absolute values of the difference values are larger than zero. The difference evaluation value calculation unit 332 adopts the counted number as a difference evaluation value. Here, the difference evaluation value calculation unit 332 may count the number of coordinates at which the absolute values are larger than a threshold that is set in advance. The threshold is set in advance in accordance with characteristics of the image sensor or the like.

Meanwhile, the difference evaluation value calculation unit 332 may detect high contrast components from each of the in-vivo image of the determination target frame and the in-vivo image of the previous frame, binarize the high contrast components, and count the number of pixels at which difference values between the frames are larger than zero, or may calculate absolute errors or square errors between the in-vivo image of the determination target frame and the in-vivo image of the previous frame, binarize the calculated errors, and count the number of pixels at which difference values between the frames are larger than zero, instead of the counted number as described above. Meanwhile, the high contrast components are, for example, edge components, and may be detected by using a known detection method, such as Prewitt filter or Sobel filter.

The luminance evaluation value calculation unit 34 calculates a luminance evaluation value on the basis of luminance values in the determination target frame. Specifically, the luminance evaluation value calculation unit 34 reduces an in-vivo image corresponding to an imaging signal, calculates an average value of luminance values in the reduced in-vivo image, and adopts the average value as a luminance calculated value. Meanwhile, instead of reduction, it may be possible to read pixel values in a certain line and calculate an average value of the read pixel values. The luminance evaluation value calculation unit 34 calculates an average value of pixel values of certain pixels after performing decimation on all of the pixels included in the in-vivo image. Further, the luminance evaluation value calculation unit 34 may calculate an average value of all of luminance values in the in-vivo image of the determination target frame, and adopts the average value as the luminance evaluation value. Furthermore, the luminance evaluation value calculation unit 34 may set a plurality of calculation regions in the in-vivo image, calculate an average value of luminance values of pixels included in each of the calculation regions, and adopts the average value as the luminance evaluation value. If the plurality of calculation regions are set, it is preferable to set the regions in a central part and edge parts of the image in terms of reflecting luminance values of the entire image. Further, the luminance evaluation value calculation unit 34 may set a threshold for the luminance values and exclude luminance values smaller than the threshold or luminance values larger than the threshold from average value calculation targets. The luminance evaluation value calculation unit 34 is configured with a general-purpose processor, such as a CPU, or a dedicated processor including various arithmetic circuits, such as an ASIC, that execute specific functions.

The execution determination unit 35 determines whether to perform defective pixel detection in the determination target frame, by using the motionlessness determination value (the motion evaluation value and the difference evaluation value) and the luminance evaluation value that are calculated by the motionlessness determination value calculation unit 33 and the luminance evaluation value calculation unit 34. If the in-vivo image is not in a dark state and represents a motionless scene, that is, if it is determined that the subject has not moved between frames, the execution determination unit 35 determines that the defective pixel detection is not to be performed. Here, the dark state indicates a state in which a luminance value of the entire image is small, a subject is not drawn, and the image is in a dark (black) state. The motionless scene may occur at the time of resolution evaluation in an endoscope, for example. When the resolution evaluation is performed, a chart in which a black line or a black character is drawn on a white background is captured. In this case, the same captured image is successively captured in a plurality of frames. As described above, a scene in which images are not changed is referred to as the motionless scene. The execution determination unit 35 is configured with a general-purpose processor, such as a CPU, or a dedicated processor including various arithmetic circuits, such as an ASIC, that execute specific functions.

It is possible to distinguish among the motionless scene, a flat image, and an image with motion from the motion evaluation value (motion vector) calculated by the motion evaluation value calculation unit 331. Further, it is possible to distinguish among the motionless scene, the flat image, and the image with motion from the difference evaluation value calculated by the difference evaluation value calculation unit 332. The flat image described here indicates an image in which a degree of irregularities or texture of an entire subject is uniform and in which a flat subject whose color change is small between frames is captured. In the present embodiment, it is explained that the motionless scene, the flat image, and the image with motion are separately evaluated by using the motion evaluation value and the difference evaluation value, but it may be possible to distinguish among the motionless scene, the flat image, and the image with motion by using only the motion evaluation value.

FIG. 3 is a diagram for explaining execution determination performed by the motionlessness determination unit of the processing device according to one embodiment of the present disclosure. The execution determination unit 35 determines whether a captured in-vivo image represents a motionless scene from a motionlessness determination value. As in a table illustrated in FIG. 3, if both of the motion evaluation value and the difference evaluation value are zero, the execution determination unit 35 determines that the in-vivo image is an image of the motionless scene. Further, if the motion evaluation value is equal to or larger than 1 and the difference evaluation value is zero, the execution determination unit 35 determines that the in-vivo image is not an image of the motionless scene, but an image in which a flat subject is captured. Furthermore, if both of the motion evaluation value and the difference evaluation value are equal to or larger than 1, the execution determination unit 35 determines that the subject is moving in the in-vivo image (the image with motion).

Moreover, the execution determination unit 35 determines whether the in-vivo image is in a dark state on the basis of the luminance evaluation value. If the luminance evaluation value is equal to or smaller than an execution determination threshold that is set in advance, the execution determination unit 35 determines that the in-vivo image is in the dark state. In contrast, if the luminance evaluation value is larger than the threshold, the execution determination unit 35 determines that the in-vivo image is in a bright state in which a subject is drawn.

The execution determination unit 35 determines whether to perform the defective pixel detection in the determination target frame on the basis of a determination result based on the motionlessness determination value and a determination result based on the luminance evaluation value. If the in-vivo image is in the bright state and represents the motionless scene, the execution determination unit 35 determines that the defective pixel detection is not to be performed. In contrast, if the in-vivo image is in the dark state and does not represent the motionless scene, the execution determination unit 35 determines that the defective pixel detection is to be performed. The execution determination unit 35 outputs a determination result to the control unit 40.

Meanwhile, if it is determined that the in-vivo image is in the dark state from the luminance evaluation value, the execution determination unit 35 may determine that the defective pixel detection is to be performed regardless of the motion evaluation value and the difference evaluation value.

The buffer 36 stores therein imaging signals processed by the imaging signal processing unit 31, for set frames. In the present embodiment, explanation will be given based on the assumption that a plurality of frames are stored. The buffer 36 stores therein imaging signals for a several frames in order from the latest generation (acquisition) time while sequentially updating the imaging signals, e.g., if a new imaging signal is input, the buffer 36 overwrites an oldest imaging signal among currently-stored imaging signals with the new imaging signal. The buffer 36 is configured with a rewritable memory, such as a random access memory (RAM).

If the execution determination unit 35 determines that the defective pixel detection is to be performed, the detection unit 37 reads an in-vivo image (imaging signal) of a target frame from the buffer 36, and performs a defective pixel detection process on the read in-vivo image. The detection unit 37 includes a filtering processing unit 371, a variance calculation unit 372, a difference value calculation unit 373, and a defect determination unit 374. The detection unit 37 is configured with a general-purpose processor, such as a CPU, or a dedicated processor including various arithmetic circuits, such as an ASIC, that execute specific functions.

The filtering processing unit 371 performs an order statistic filtering process on the in-vivo image of the target frame. Specifically, the filtering processing unit 371 performs the order statistic filtering process using a median filter.

Figure 6:
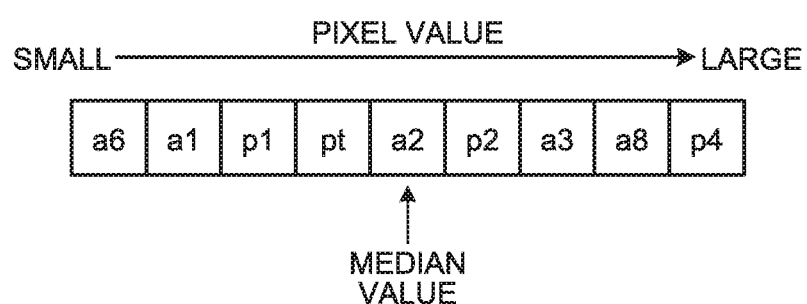
FIG. 6 is a diagram for explaining the filtering process performed by the filtering processing unit of the processing device according to one embodiment of the present disclosure.

FIG. 4 to FIG. 6 are diagrams for explaining the filtering process performed by the filtering processing unit of the processing device according to one embodiment of the present disclosure. In a block of 9 pixels such as a pixel of interest pt indicated by hatching and neighboring pixels (a pixel p1 to a pixel p8 enclosed by a solid line) as illustrated in FIG. 4 for example, the filtering processing unit 371 performs the order statistic filtering process on each of the pixel of interest pt and the neighboring pixels. Meanwhile, the filtering processing unit 371 may adopt a rank order filter, a-trimmed mean filter, or a double window modified trimmed mean filter, instead of the median filter.

More specifically, as illustrated in FIG. 5, if the pixel of interest pt is set, the filtering processing unit 371 sorts pixel values of pixels of 3×3(=9) centered at each of the pixel of interest pt and the neighboring pixels by magnitudes of the pixel values, and outputs a median (median value) as a pixel value of each of the pixels. For example, when the filtering process is performed on the pixel p1, the filtering processing unit 371 performs the process using pixel values in a pixel region centered at the pixel p1. As illustrated in FIG. 6, the filtering processing unit 371 performs sorting in accordance with the magnitude of the pixel value of each of the pixels and outputs a median value. The output pixel value is a value of the pixel p1 subjected to the order statistic filtering process. The filtering processing unit 371 performs the above-described order statistic filtering process on all of pixel positions on the in-vivo image.

If the imaging element 244 has what is called Bayer arrangement, the order statistic filtering process is performed on pixels at which color filters of the same color are arranged. Further, in this example, the median value is output including the pixel of interest in the order statistic filtering process, but it may be possible not to use the pixel of interest. In this case, the number of pixels is changed to 8, and therefore, an average value between a forth pixel value and a fifth pixel value from the smallest pixel value is adopted as a value of the median value.

Figure 7:
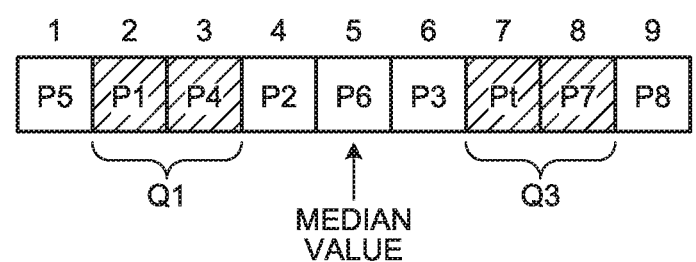
FIG. 7 is a diagram for explaining a process performed by a variance calculation unit of the processing device according to one embodiment of the present disclosure.

The variance calculation unit 372 calculates variance of the pixel value of the pixel of interest before and after the order statistic filtering process. FIG. 7 is a diagram for explaining a process performed by the variance calculation unit of the processing device according to one embodiment of the present disclosure. The variance calculation unit 372 calculates an interquartile range as statistical variance. The interquartile range indicates variance of a distribution in a case where a median value is adopted as a representative value of the distribution. As illustrated in FIG. 7, the variance calculation unit 372 sorts pixel values (Pt and P1 to P8) of the pixel of interest pt and the neighboring pixels (the pixel p1 to the pixel p8) subjected to the order statistic filtering process in accordance with the magnitude of each of the pixels. The variance calculation unit 372 further obtains median values of pixel value groups, in each of which four pixels are present, on both sides of the median value (the pixel value P6) as a result of the sorting. The number of pieces of data in each of the pixel value groups is four; therefore, the variance calculation unit 372 adopts, as the median values of the respective pixel value groups, an average value between the second and the third pixel values (the pixel values P1 and P4) from the smallest pixel value and an average value between the seventh and the eighth pixel values (the pixel values Pt and P7) from the smallest pixel value. The variance calculation unit 372 calculates the interquartile range (IQR) from the median value of each of the pixel value groups. Specifically, assuming that the average value between the second and the third pixel values (the pixel values P1 and P4) is denoted by Q1 and the average value of the seventh and the eighth pixel values (the pixel values Pt and P7) is denoted by Q3, the variance calculation unit 372 adopts a difference that is obtained by subtracting Q1 from Q3 as the interquartile range (IQR). Meanwhile, the variance calculation unit 372 may use dispersion, standard deviation, a difference between absolute values of average values, or a range of a distribution width of pixel values, instead of the interquartile range.

The difference value calculation unit 373 calculates a difference of the pixel value of the pixel of interest before and after the order statistic filtering process. The difference value calculation unit 373 outputs the calculated difference to the defect determination unit 374.

The defect determination unit 374 obtains a determination value by dividing the difference value calculated by the difference value calculation unit 373 by the interquartile range (IQR) calculated by the variance calculation unit 372. If the obtained determination value is larger than a defect determination threshold that is set in advance, the defect determination unit 374 determines that the pixel of interest is a defective pixel. In contrast, if the obtained determination value is equal to or smaller than the threshold, the defect determination unit 374 determines that the pixel of interest is not a defective pixel.

The interquartile range indicates variance, and it is indicated that pixel values of the neighboring pixels of the pixel of interest are at the same level (flat values) if the variance is small, and the pixel values of the neighboring pixels of the pixel of interest are not flat if the variance is large. By calculating the determination value by using the interquartile range as a denominator, a defective pixel is determined if the variance is small and the pixel values of the neighboring pixels are flat. Further, if the pixel value of the pixel of interest stands out, the difference value increases; therefore, by using the difference value as a numerator, it is possible to easily determine a degree of standing out of the pixel value of the pixel of interest.

The defect determination unit 374 outputs a determination result in which a coordinate of the pixel of interest and information indicating a defect are associated to the storage unit 39.

The input unit 38 is realized by using a keyboard, a mouse, a switch, or a touch panel, and receives input of various signals, such as an operation instruction signal for giving an instruction on operation of the endoscope system 1. Meanwhile, the input unit 38 may include a switch arranged on the operation unit 22 or a portable terminal, such as an external tablet computer.

The storage unit 39 stores therein various programs for operating the endoscope system 1 and data including various parameters or the like needed for operation of the endoscope system 1. Further, the storage unit 39 stores therein identification information on the processing device 3. Here, the identification information includes unique information (ID), a model year, specification information, or the like on the processing device 3. Further, the storage unit 39 includes a defective pixel information storage unit 391 for storing information on a defective pixel. The defective pixel information storage unit 391 stores therein, for example, a defective pixel map in which a defective pixel detected by the detection unit 37 is mapped on pixel arrangement of the imaging element 244, for example. The defective pixel information storage unit 391, upon acquiring a determination result from the defect determination unit 374, updates the defective pixel map in accordance with the determination result.

Furthermore, the storage unit 39 stores therein various programs including an image acquisition processing program for performing an image acquisition processing method in the processing device 3. The various programs may be recorded in a computer-readable recording medium, such as a hard disk, a flash memory, a CD-ROM, a DVD-ROM, or a flexible disk, and widely distributed. Meanwhile, the various programs as described above may be acquired by download via a communication network. The communication network described here is realized by, for example, a known public line network, a local area network (LAN), a wide area network (WAN), or the like, regardless of whether it is wired or wireless.

The storage unit 39 configured as described above is realized by using a read only memory (ROM) in which various programs or the like are installed in advance, a RAM or a hard disk for storing calculation parameters, data, or the like for each of processes, or the like.

The control unit 40 controls drive of each of structural units including the imaging element 244 and the light source unit 3a and controls input and output of information to and from each of the structural units. The control unit 40 refers to control information data (for example, a read timing or the like) that is stored in the storage unit 39 and that is used to control imaging, and transmits the control information data as a driving signal to the imaging element 244 through a predetermined signal line that is included in the assembly cable 245. The control unit 40 is configured with a general-purpose processor, such as a CPU, or a dedicated processor including various arithmetic circuits, such as an ASIC, that execute specific functions.

Next, a configuration of the light source unit 3a will be described. The light source unit 3a includes an illumination unit 301 and an illumination control unit 302. The illumination unit 301 emits illumination light at different exposures to an object (subject) in a sequentially switching manner, under the control of the illumination control unit 302. The illumination unit 301 includes a light source 301a and a light source driver 301b.

The light source 301a is configured with an LED light source that emits white light, one or more lenses, and the like, and emits light (illumination light) by drive of the LED light source. The illumination light generated by the light source 301a is emitted to the object from a distal end of the distal end portion 24 via the light guide 241. Further, the light source 301a may be realized by using any of a laser light source, a xenon lamp, a halogen lamp, and the like, instead of the LED light source.

The light source driver 301b supplies electric current to the light source 301a and causes the light source 301a to emit illumination light, under the control of the illumination control unit 302.

The illumination control unit 302 controls an amount of electricity to be supplied to the light source 301a and controls a driving timing of the light source 301a, on the basis of a control signal (light adjustment signal) from the control unit 40.

The display device 4 displays a display image corresponding to the image signal that is received from the processing device 3 (the display image generation unit 32) via a video cable. The display device 4 is configured with a monitor made with liquid crystal, organic electro luminescence (EL), or the like.

Next, the defective pixel detection process performed by the endoscope system 1 will be described. FIG. 8 is a flowchart illustrating image processing performed by the processing device according to one embodiment of the present disclosure. In the endoscope system 1, if the processing device 3 acquires an imaging signal, a display image corresponding to the acquired imaging signal is displayed on the display device 4, and a defective pixel detection execution determination and a defective pixel detection process are performed. The flowchart illustrated in FIG. 8 indicates the flow of the defective pixel detection process in a case where the defective pixel detection execution determination and the defective pixel detection are to be performed. In the following, explanation will be given based on the assumption that each of the units operates under the control of the control unit 40.

The motionlessness determination value calculation unit 33, upon acquiring an imaging signal from the imaging signal processing unit 31, performs a motion evaluation value calculation process (Step S101) and a difference evaluation value calculation process (Step S102) (motionlessness determination value calculation step).

At Step S101, the motion evaluation value calculation unit 331 calculates a motion vector of a subject in a determination target frame with respect to a previous frame by using an in-vivo image of the determination target frame and an in-vivo image of the previous frame, and adopts a magnitude of the vector as the motion evaluation value.

At Step S102, the difference evaluation value calculation unit 332 calculates a difference value of pixel values (luminance values) at the same coordinates in the in-vivo image of the determination target frame and the in-vivo image of the previous frame for each of pixels (coordinates). The difference evaluation value calculation unit 332 counts the number of coordinates at which the difference values are larger than zero, and adopts the counted number as the difference evaluation value.

At Step S103, the luminance evaluation value calculation unit 34 calculates the luminance evaluation value on the basis of luminance values in the determination target frame (luminance evaluation value calculation step). As described above, the luminance evaluation value calculation unit 34 reduces the in-vivo image, calculates an average value of luminance values in the reduced in-vivo image, and adopts the average value as the luminance calculated value.

Meanwhile, Steps S101 to S103 as described above may be performed in a reverse order, Step S102 may be performed first, or Steps S101 to S103 may be performed in a parallel manner.

If the motion evaluation value, the difference evaluation value, and the luminance evaluation value are calculated at Steps S101 to S103, the execution determination unit 35 determines whether to perform defective pixel detection in the determination target frame on the basis of a determination result based on the motionlessness determination value and a determination result based on the luminance evaluation value (Step S104: execution determination step).

If the in-vivo image is in the bright state and represents a motionless scene on the basis of the determination results, the execution determination unit 35 determines that the defective pixel detection is not to be performed. If the execution determination unit 35 determines that the defective pixel detection is not to be performed (Step S104: No), the control unit 40 terminates the defective pixel detection process on the determination target frame. Thereafter, the control unit 40 may perform the defective pixel detection process on a next frame or terminates the defective pixel detection process if an image of a next frame is not received.

In contrast, if the execution determination unit 35 determines that the defective pixel detection is to be performed (Step S104: Yes), the control unit 40 proceeds to Step S105.

At Step S105, the filtering processing unit 371 performs the order statistic filtering process on the in-vivo image of the target frame.

At Step S106 following Step S105, the variance calculation unit 372 calculates variance of the pixel value of the pixel of interest before and after the order statistic filtering process.

At Step S107, the difference value calculation unit 373 calculates a difference of the pixel value of the pixel of interest before and after the order statistic filtering process.

Meanwhile, Steps S106 and S107 as described above may be performed in a reverse order or may be performed in a parallel manner.

At Step S108 following Step S107, the defect determination unit 374 obtains a determination value by dividing the difference value calculated by the difference value calculation unit 373 by the interquartile range (IQR) calculated by the variance calculation unit 372. The defect determination unit 374 determines whether the determination target pixel (pixel of interest) is a defective pixel from the obtained determination value (detection step). If the obtained determination value is larger than the defect determination threshold, the defect determination unit 374 determines that the pixel of interest is a defective pixel. In contrast, if the obtained determination value is equal to or smaller than the threshold, the defect determination unit 374 determines that the pixel of interest is not a defective pixel.

The detection unit 37 performs the processes from Steps S105 to S108 as described above on at least pixels that are included in the in-vivo image, and determines whether each of the pixels is a defective pixel. If the defective pixel determination process on all of the pixels is terminated, the defect determination unit 374 outputs a determination result in which the coordinate of the pixel of interest and information on a defect are associated to the storage unit 39.

At Step S109, upon acquiring the determination result from the defect determination unit 374, the defective pixel information storage unit 391 updates the defective pixel map.

In the present embodiment as described above, whether to perform the defective pixel detection process is determined on the basis of a motion of a subject in an image, a difference between corresponding pixels, and each of evaluation values on luminance of the image. In the present embodiment, the defective pixel detection process is not performed in the motionless scene; therefore, even if a pixel that is erroneously determined as a defective pixel is present, it is possible to reverse the determination at a later time. According to the present embodiment, even when an endoscope acquires an image of a motionless scene in which a subject is motionless, it is possible to appropriately determine a pixel defect.

Meanwhile, in the present embodiment as described above, it is explained that the imaging signal processing unit 31 generates a processing signal including an image in which RGB color components are given, but it may be possible to generate a processing signal that has a YCbCr color space including a luminance (Y) component and color difference components on the basis of the YCbCr color space, or it may be possible to generate a processing signal in which a color component and a luminance component are separated by using the HSV color space formed of three components of hue, saturation (Saturation Chroma), and lightness (Value Lightness Brightness), the L*a*b* color space using a three-dimensional space, or the like.

Furthermore, in the embodiment as described above, it is explained that a simultaneous lighting/imaging system is adopted in which the light source unit 3a emits white illumination light including RGB color components and the light receiving unit 244a receives reflected light of the illumination light, but it may be possible to adopt a frame sequential lighting/imaging system in which the light source unit 3a separately and sequentially emits light of a plurality of color components and the light receiving unit 244a receives light of each of the color components.

Moreover, in the embodiment as described above, it is explained that the light source unit 3a is configured separately from the endoscope 2, but it may be possible to arrange a light source device in the endoscope 2 by, for example, arranging a semiconductor light source at a distal end of the endoscope 2. In addition, it may be possible to add the functions of the processing device 3 to the endoscope 2.

Furthermore, in the embodiment as described above, it is explained that the light source unit 3a is integrated with the processing device 3, but the light source unit 3a and the processing device 3 may be separated and the illumination unit 301 and the illumination control unit 302 may be arranged outside the processing device 3, for example. In addition, the light source 301a may be arranged at the distal end of the distal end portion 24.

Moreover, in the embodiment as described above, it is explained that the endoscope system according to the present disclosure is the endoscope system 1 using the flexible endoscope 2 that adopts a living tissue or the like inside a subject as an observation object, but it may be possible to adopt an endoscope system in which a camera head is connected to an eyepiece portion of a rigid endoscope, an industrial endoscope for observing material properties, a capsule endoscope, a fiberscope, or an optical endoscope, such as an optical viewing tube.

Furthermore, in the embodiment as described above, the endoscope system has been described as an example, but the technology is also applicable to a case in which a video is output to an electronic viewfinder (EVF) that is arranged on a digital still camera or the like, for example.

INDUSTRIAL APPLICABILITY

As described above, the image processing apparatus, the image processing method, and the image processing program according to the present disclosure is useful for appropriately determining a pixel defect even when an endoscope captures an image of a motionless scene in which a subject is motionless.

According to the present disclosure, it is possible to appropriately determine a pixel defect even when an endoscope captures an image of a motionless scene in which a subject is motionless.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus that performs a process on an image that is captured by an endoscope introduced in a subject, the image processing apparatus comprising a processor comprising hardware, the processor being configured to:
   calculate, a motion evaluation value on a motion of a subject in a determination target frame by using an image of the determination target frame and an image of a frame for which an acquisition time is different from an acquisition time of the determination target frame;
   calculate a difference between a pixel value in the image of the determination target frame and a pixel value in the image of the frame for which the acquisition time is different from the acquisition time of the determination target frame to acquire a difference evaluation value of the determination target frame;
   determine whether to perform defective pixel detection on the image of the determination target frame by using the motion evaluation value and the difference evaluation value; and
   when it is determined that the defective pixel detection is to be performed, detect a defective pixel by determining whether a pixel of interest that is a determination target is a defective pixel with respect to the image of the determination target frame, based on a pixel value of the pixel of interest and pixel values of neighboring pixels that are located in a vicinity of the pixel of interest.

2. The image processing apparatus according to claim 1, wherein the processor is further configured to
   calculate a luminance evaluation value based on a luminance value in each of the images of the plurality of frames, and
   determine that the defective pixel detection is to be performed if the image of the determination target frame is in a dark state based on the luminance evaluation value.

3. The image processing apparatus according to claim 1, wherein the processor is further configured to
   detect high contrast components from each of the image of the determination target frame and the image of the frame for which the acquisition time is different from the acquisition time of the determination target frame,
   binarize the detected high contrast components, and
   adopt, as the difference evaluation value, a counted number that is obtained by counting a number of pixels for which difference values between the frames are larger than zero.

4. The image processing apparatus according to claim 2, wherein the processor is further configured to adopt, as the luminance evaluation value, an average value of pixel values of certain pixels after performing decimation on all of pixels included in the image.

5. The image processing apparatus according to claim 1, wherein the processor is further configured to determine whether the pixel of interest is a defective pixel based on:
   a difference value between a median value and the pixel value of the pixel of interest or a difference value between an average value and the pixel value of the pixel of interest, wherein the median value and the average value being of the pixel value of the pixel of interest and the pixel values of the neighboring pixels, and
   on variance of the pixel value of the pixel of interest before and after order statistic filtering.

6. An image processing method of performing a process on an image that is captured by an endoscope introduced into a subject, the image processing method comprising:
   calculating, a motion evaluation value on a motion of a subject in a determination target frame by using an image of the determination target frame and an image of a frame for which an acquisition time is different from an acquisition time of the determination target frame;
   calculating a difference between a pixel value in the image of the determination target frame and a pixel value in the image of the frame for which the acquisition time is different from the acquisition time of the determination target frame to acquire a difference evaluation value of the determination target frame;
   determining whether to perform defective pixel detection on the image of the determination target value by using the motion evaluation value and the difference evaluation value; and
   in a case where it is determined that the defective pixel detection is to be performed at the determining, detecting a defective pixel by determining whether a pixel of interest that is a determination target is a defective pixel with respect to the image of the determination target frame, based on a pixel value of the pixel of interest and pixel values of neighboring pixels that are located in a vicinity of the pixel of interest.

7. A non-transitory computer-readable recording medium with an executable program stored thereon, the program causing an image processing apparatus configured to perform a process on an image that is captured by an endoscope introduced in a subject, to execute:
- calculating, a motion evaluation value on a motion of a subject in a determination target frame by using an image of the determination target frame and an image of a frame for which an acquisition time is different from an acquisition time of the determination target frame;
- calculating a difference between a pixel value in the image of the determination target frame and a pixel value in the image of the frame for which the acquisition time is different from the acquisition time of the determination target frame to acquire a difference evaluation value of the determination target frame;
- determining whether to perform defective pixel detection on the image of the determination target value by using the motion evaluation value and the difference evaluation value; and
- in a case where it is determined that the defective pixel detection is to be performed at the determining, detecting a defective pixel by determining whether a pixel of interest that is a determination target is a defective pixel with respect to the image of the determination target frame, based on a pixel value of the pixel of interest and pixel values of neighboring pixels that are located in a vicinity of the pixel of interest.

* * * * *